United States Patent [19]

Guinosso

[11] Patent Number: 4,535,168
[45] Date of Patent: Aug. 13, 1985

[54] PREPARATION OF INDOLINE-2-CARBOXYLIC ACID VIA THE INTERMEDIATE INDOLINE-2-CARBOXYLIC ACID ESTER TIN COMPLEX

[75] Inventor: Charles J. Guinosso, King of Prussia, Pa.

[73] Assignee: American Home Products Corporation, New York, N.Y.

[21] Appl. No.: 463,430

[22] Filed: Feb. 3, 1983

[51] Int. Cl.$^3$ .............................................. C07D 209/18
[52] U.S. Cl. ..................................... 548/402; 548/491
[58] Field of Search ................................. 548/402, 491

[56] References Cited

PUBLICATIONS

Hudson et al., "The Synthesis and Chemistry of DL-Indoline-2-Carboxylic Acid", Aust. J. Chem., 20, 1935–1941 (1967).
Corey et al., "Studies in Asymmetric Synthesis of α-Amino Acids", J. Am. Chem. Soc., 92, 2476, 2480 (1970).
Robinson, B., "The Reduction of Indoles and Related Compounds", Chem. Reviews, 69, 785, 785–787 (1969).
Elderfield, R. C., ed., *Heterocyclic Compounds*, vol. 3, pp. 46–51, (John Wiley & Sons, Inc., New York, 1952).

*Primary Examiner*—Glennon H. Hollrah
*Assistant Examiner*—D. B. Springer
*Attorney, Agent, or Firm*—Arthur G. Seifert

[57] ABSTRACT

Disclosed herein is a process for preparing indoline-2-carboxylic acids from the corresponding indole-2-carboxylic acid or ester in which the indole-2-carboxylic acid or ester is first reduced to the indoline-2-carboxylic acid ester tin complex using stannous chloride and dry hydrogen chloride gas in a lower alkanol solvent at atmospheric pressures; and the resulting tin complex, dissolved in a lower alkanol, is converted directly to the free indoline-2-carboxylic acid by treatment with aqueous potassium or sodium hydroxide. The aqueous hydroxide treatment may take place in situ or after first isolating the intermediate indoline-2-carboxylic acid ester tin complex.

4 Claims, No Drawings

PREPARATION OF INDOLINE-2-CARBOXYLIC ACID VIA THE INTERMEDIATE INDOLINE-2-CARBOXYLIC ACID ESTER TIN COMPLEX

Indoline-2-carboxylic acids are used as the starting material in the preparation of N-(3-mercapto-2-alkyl-1-oxopropyl)-2,3-dihydro-1H-indole-2-carboxylic acids and N-(2-[[1-(ethoxycarbonyl)-3-phenylpropyl]amino]-1-oxopropyl)-2,3-dihydro-1H-indole-2-carboxylic acids which exhibit pharmacological properties as angiotensin converting enzyme inhibitors (ACE) and as antihypertensive agents, as shown in U.S. Pat. Nos. 4,303,583 and 4,350,633, respectively.

Indoline-2-carboxylic acid was first described by Hudson and Robertson in the Australian Journal of Chemistry, 20, 1935 (1967). They obtained indoline-2-carboxylic acid by first reducing indole-2-carboxamide using phosphonium iodide and fuming hydriodic acid and then hydrolyzing the resulting indoline-2-carboxamide.

Subsequently, Corey et al., Journal of the American Chemical Society, 92, 2476-2488 (1970) described the reduction of indole-2-carboxylic acid ethyl ester to obtain indoline-2-carboxylic acid ethyl ester. Corey et al. used metallic tin and dry hydrogen chloride gas in ethanol in a high pressure sealed bomb to effect the reduction. In this method, the indoline-2-carboxylic acid ethyl ester is obtained first as a tin complex which is isolated and then treated with anhydrous ammonia to obtain the free ester. This ester must then be hydrolyzed in order to obtain the free acid desired as starting materials in the production of the described ACE inhibitors.

The preparation of indoline-2-carboxylic acids via the Corey et al. process thus has a number of drawbacks for both commercial and laboratory use. In the reduction step, a cumbersome sealed bomb is required due to the use of tin metal and excess hydrogen chloride gas (which generates hydrogen gas). Additionally, two steps are necessary to obtain the desired indoline-2-carboxylic acid from the indoline-2-carboxylic acid ester tin complex, which must first be isolated and washed. The treatment of the tin complex with anhydrous ammonia is also a cumbersome step since dry reagents must be used. In practice, it is difficult to remove all the tin from the ester even when dry conditions have been carefully maintained.

Applicant, on the other hand, has invented a reduction of indole-2-carboxylic acid to the indoline-2-carboxylic acid which does not require tin metal or a sealed bomb. In Applicant's process, stannous chloride, a less powerful reducing agent than tin metal, is used and the reduction is carried out at atmospheric conditions even though the reducing agent is less powerful.

Additionally, Applicant has invented a process for readily obtaining substantially tin free indoline-2-carboxylic acid directly from the indoline-2-carboxylic acid ester tin complex. In Applicant's process, potassium or sodium hydroxide, in water, is used to break up the tin complex. Surprisingly, this process yields indoline-2-carboxylic acid of high purity directly. Moreover, Applicant's treatment of the indoline-2-carboxylic ester tin complex with potassium or sodium hydroxide may be practiced without first isolating the tin complex, thereby allowing the use of one reaction vessel from start to finish and eliminating the formation of corrosive tin chlorides during the drying of the isolated tin complex. Accordingly, Applicant's entire process for the preparation of indoline-2-carboxylic acids utilizes only two main steps which may be carried out in the same reaction vessel and gives constant overall yields of 80-92%.

DETAILED DESCRIPTION OF THE INVENTION

The first aspect of the present invention is a process for producing an indoline-2-carboxylic acid ester tin complex of the formula:

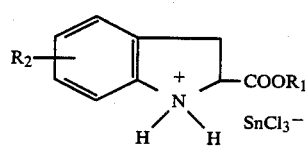

II wherein $R_1$ is alkyl of 1-4 carbon atoms and $R_2$ is hydrogen, alkyl of 1-4 carbon atoms, alkoxy of 1-4 carbon atoms, or halogen, which process comprises contacting an indole-2-carboxylic acid or ester of the formula:

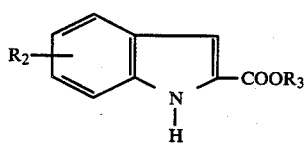

I wherein $R_3$ is hydrogen or $R_1$ (defined above) and $R_2$ is as defined above, with dry hydrogen chloride gas and stannous chloride in an alkanol of the formula $R_1OH$ at atmospheric pressures for a period of 2 to 24 hours at temperatures between $-25°$ C. and $+25°$ C.

In this aspect of the invention, $R_2$ is hydrogen and $R_3$ is hydrogen, methyl or ethyl are independently preferred. Thus, $R_1$ is methyl or ethyl are also preferred.

The second aspect of this invention is a process for converting the resulting indoline-2-carboxylic acid ester tin complex to the indoline-2-carboxylic acid in one main step. This process comprises contacting the tin complex, dissolved in an alkanol solvent of 1-3 carbon atoms with an aqueous potassium or sodium hydroxide solution. The resulting solution is then acidified in order to obtain the free acid.

In this aspect of the invention, $R_2$ is hydrogen and $R_1$ is methyl or ethyl are, independently, preferred. Methanol or ethanol are the preferred alkanol solvents. The tin complex may first be isolated from the reduction mixture before treatment with the aqueous potassium or sodium hydroxide solution, or it may be treated in situ in the reduction mixture.

The third and most advantageous aspect of the invention is a process for obtaining an indoline-2-carboxylic acid from the corresponding indole-2-carboxyic acid or ester employing two main steps. This process comprises first contacting the indole-2-carboxylic acid or ester of the formula:

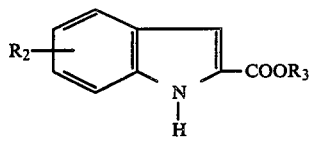

wherein $R_2$ is hydrogen, alkyl of 1–4 carbon atoms, alkoxy of 1–4 carbon atoms, or halogen and $R_5$ is hydrogen or $R_1$ ($R_1$ being alkyl of 1–4 carbon atoms), with dry hydrogen chloride gas and stannous chloride in an alkanol of the formula $R_1OH$ at atmospheric pressures for a period of 2 to 24 hours at temperatures between $-25°$ C. and $+25°$ C. The resulting indoline-2-carboxylic acid ester tin complex of the formula:

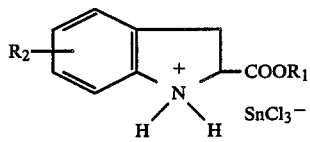

wherein $R_1$ and $R_2$ are as defined above, is then contacted with an aqueous potassium or sodium hydroxide solution, in an alkanol solvent of 1–3 carbon atoms. The remaining solution is then acidified in order to obtain the free acid.

The second step of this process may be carried out in the solution of the completed reduction step (i.e. in situ) or the second step may be carried out after isolating the tin complex. In the latter case, the tin complex is preferably not dried. In this aspect of the invention, $R_2$ is hydrogen and $R_3$ is hydrogen, methyl or ethyl are, independently, preferred. Methanol or ethanol are the preferred solvents in step b.

As used herein, "halogen" refers to fluorine, chlorine and bromine, of which chlorine is preferred. Alkyl and alkoxy groups of 1 or 2 carbon atoms are preferred with respect to $R_2$.

The stannous chloride reduction is preferably begun by first dissolving the hydrogen chloride gas in the absolute ethanol while maintaining the temperature at about $-20°$ C. This dissolution is exothermic. The indole-2-carboxylic acid (or ester) and then the stannous chloride (2–3 moles per mole of indole) are next added to separate portions, after which the temperature is allowed to rise to 0° C. (about 30 minutes). The reaction is then preferably cooled in an ice bath and the temperature allowed to rise slowly to about 16° C. over the next 3.5 hours (to a light green partial solution) and then to room temperature in another 12 hours (overnight). At the end of this time, the solution is light green, and thin layer chromatography shows the absence of starting material.

In order to isolate the indoline-2-carboxylic acid ester tin complex formed by the reduction, the reaction solution is first concentrated and then allowed to sit for 2–3 hours at room temperature and then 2–3 hours at 5° C. The crystalline tin complex is then filtered out, washed and dried.

If, instead, it is desired to convert the indoline-2-carboxylic acid ester tin complex directly to the free carboxylic acid, then the light green reaction solution is concentrated, preferably on a rotary evaporator keeping the bath temperature less than 30° C. The remaining solution will then have an orange color. The solution is then chilled to about 20° C. and the aqueous potassium or sodium hydroxide is added dropwise to the vigorously stirred solution over a period of 1–4 hours, adding additional ethanol if needed to keep the suspension fluid. (The addition of the hydroxide is exothermic). When the temperature is maintained at 20°–25° C., the conversion is completed in 2–5 hours. During the addition of the hydroxide, the pH is adjusted to 9 or above and preferably to 11 or above. The mixture may be stirred for a further period after this portion of hydroxide has been added. During this period, further hydroxide may need to be added to adjust the pH to 11.

The white solid (tin hydroxides) is filtered out and the ethanol is evaporated fom the alkaline filtrate (pH 11 by pH meter) on a rotary evaporator at less than 30° C. Water is then added to the pH reduced to 7. This solution is filtered again, if necessary, and the pH thereafter reduced to about 5. The mixture is then chilled in an ice-bath for about 2 hours to precipitate the indoline-2-carboxylic acid product of the formula:

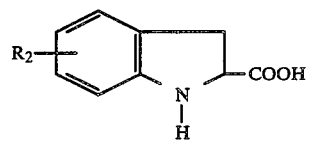

wherein $R_2$ is as defined above.

The following examples further illustrate the practice of the invention and the best mode for carrying out the invention:

EXAMPLE 1

Indoline-2-Carboxylic Acid

A three-neck, 3-liter round bottom flask equipped with a mechanical stirrer, water condenser and gas inlet tube was charged with 1000 ml. of absolute ethanol. The ethanol was saturated with dry hydrogen chloride gas (687 g.; 18.85 moles) at $-20°$ C. (dry-ice acetone bath). Indole-2-carboxylic acid (100 g.; 0.62 moles) was added, followed by anhydrous stannous chloride (340 g.; 1.79 moles). The temperature of the reaction mixture was allowed to rise slowly over 2 hours to 0° C. The dry-ice acetone bath was replaced with an ice bath and the reaction mixture was gently stirred overnight.

Approximately 200 ml. of ethanol were removed by distillation on a rotary evaporator under reduced pressure with the bath temperature below 30° C. The residual solution was transferred into a 5-liter flask equipped with a mechanical stirrer, then chilled to 20° C. using an ice bath. Aqueous potassium hydroxide solution that was prepared by dissolving 660 g. (10 moles) potassium hydroxide (87%) pellets in water to a total volume of 860 ml. was added dropwise with vigorous stirring over 1 hour. During the addition, the temperature of the reaction mixture was maintained between 20°–25°. The resulting mixture was stirred for 5 hours, then filtered through a bed of celite. The filtrate was stored in a refrigerator over a weekend and an additional solid that separated was removed by filtration. The filtrate was evaporated on a rotary evaporator under reduced pressure, keeping the temperature of the bath below 30° C. The residue was dissolved in water (600 ml.), the pH of the solution was adjusted to 7.0 by addition of dilute (6N) hydrochloric acid and the solution was filtered through a bed of celite to remove a fine, brown precipitate. The filtrate was acidified with dilute (6N) hydrochloric acid to pH 5 and chilled in an ice bath for 2 hours. The precipitate that separated was collected on a filter and dried over phosphorous pentoxide in vacuo overnight at 60° to give the title compound (87.1 g., 86% yield), m.p. 163°–166° C. (dec.). The analytical sample that was prepared by recrystallization from ethanol melted at 168°–170° C. with decomposition.

Analysis for: $C_9H_9NO_2$ Calculated: C, 66.24; H, 5.56; N, 8.58 Found: C, 66.06; H, 5.56; N, 8.62.

EXAMPLE 2

Indoline-2-Carboxylic Acid

A 3 liter, 4-neck flask, fitted with a stirrer, low temperature thermometer, nitrogen inlet, reflux condenser and gas inlet tube was charged with 1 liter of ethanol 2B and then cooled to −20° C. with a dry ice/acetone bath controlled on a pneumatic jack. With vigorous stirring and continuous, sufficient cooling, anhydrous hydrogen chloride gas (800 g.; 22 moles) was dissolved in the ethanol over a period of about 2 hours. With the temperature maintained at −20° C. or below, first indole-2-carboxylic acid (123 g.; 0.76 moles) and, then, anhydrous stannous chloride (400 g.; 2.12 moles) were each added all at once. The reaction mixture was maintained at −20° C. for 2 hours, then at −10° C. for 3.5 hours, and then allowed to warm to room temperature overnight. The reaction mixture was then filtered on a medium coarse sintered glass funnel to give a first crop of ethyl indoline-2-carboxylate tin chloride hydrochloride salt (154 g., wet). The wet product cake was stored in a brown bottle. The alcoholic mother liquor was transferred to a 3 liter, 1 neck, round bottom flask and concentrated on a rotary evaporator at 40° C. bath temperature to a volume of approximately 600 ml. The flask was removed from the concentrator, fitted with a stirrer and cooled under stirring to 3°–5° in an ice bath for 3 hours. The solution was again filtered on a sintered glass funnel to yield a second crop of ethyl indoline-2-carboxylic tin chloride hydrochloride salt (144 g., wet). This crop was also stored in a brown bottle until the subsequent step was begun.

A 5 liter, 4-neck flask, fitted with a stirrer, a thermometer, a reflux condenser and a dropping funnel was charged with 2.2 liters of methanol and the above two crops of ethyl indoline-2-carboxylate tin chloride hydrochloride salt were then dissolved in the methanol. 150 g. of 87% potassium hydroxide pellets were dissolved in approximately 300 ml. of water with vigorous shaking and cooling. Under vigorous stirring, the concentrated potassium hydroxide solution was added dropwise over 4 hours to the methanol solution, maintaining a pH of 11 and a temperature of 20° C. with an ice bath. The reaction mixture was stirred overnight, readjusting the pH to 11 when necessary. Then 550 ml. of water were added and the pH was adjusted to pH 9 with approximately 20 ml. of concentrated hydrochloric acid. Again adjusting the pH to 9, the solution was filtered on a Buchner funnel covered with 50 g. Celite. The pH of the solution was adjusted to 7 with about 10 ml. of concentrated HCl but no additional tin hydroxide precipitated. The methanol was then boiled off by heating the solution on a rotary evaporator (bath temperature 40±5° C.), reducing the volume of the solution to 700–800 ml. The remaining solution was then transferred to a 2 liter, 4-neck flask fitted with a stirrer, thermometer, nitrogen inlet and dropping funnel. While stirring, the ph of the solution was adjusted to 4.8 using approximately 20 ml. of concentrated hydrochloric acid. The solution was then stirred at 3°–5° C. for 2 hours. The precipitated indoline-2-carboxylic acid was filtered out, washed with 100 ml. of water, and dried overnight in a vacuum oven at 40±5° C. to a constant weight. Yield of indoline-2-carboxylic acid—100 g. (80% of theory), m.p. 155°–160° C.

What is claimed is:

1. A process for producing an indoline-2-carboxylic acid of the formula:

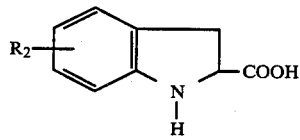

wherein $R_2$ is hydrogen, alkyl of 1–4 carbon atoms, alkoxy of 1–4 carbon atoms, or halogen, which process comprises (a) contacting an indole-2-carboxylic acid or ester of the formula:

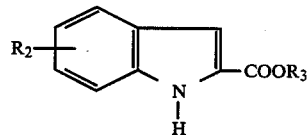

wherein $R_2$ is as defined above and $R_3$ is hydrogen or $R_1$ ($R_1$ being alkyl of 1–4 carbon atoms) with dry hydrogen chloride gas and stannous chloride in an alkanol of the formula $R_1OH$ at atmospheric pressures for a period of 2 to 24 hours at temperatures between −25° C. and +25° C., (b) contacting the resulting indoline-2-carboxylic acid ester tin complex of the formula:

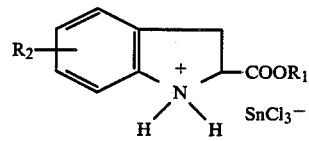

II wherein $R_1$ and $R_2$ are as defined above, which is dissolved in an alkanol solvent of 1–3 carbon atoms, with an aqueous potassium or sodium hydroxide solution, and (c) acidifying the resulting solution.

2. A process according to claim 1 wherein $R_2$ is hydrogen and $R_3$ is hydrogen, methyl or ethyl.

3. A process for claim 1 in which step (b) is carried out in situ.

4. A process according to claim 1 in which the alkanol solvent of step (b) is methanol or ethanol.

* * * * *